United States Patent [19]

Kevorkian

[11] Plant 4,617

[45] Jan. 6, 1981

[54] PEACH TREE

[76] Inventor: Aram Kevorkian, P.O. Box 409, Reedley, Calif. 93654

[21] Appl. No.: 55,026

[22] Filed: Jul. 5, 1979

[51] Int. Cl.[3] ..... A01H 5/00

[52] U.S. Cl. ..... Plt./43

[58] Field of Search ..... Plt./43

*Primary Examiner*—Robert E. Bagwill

*Assistant Examiner*—James R. Feyrer

*Attorney, Agent, or Firm*—Huebner & Worrel

[57] ABSTRACT

A peach tree, generally similar to the Redtop Peach Tree (unpatented), which bears freestone fruit having yellow flesh with red striations and which ripens from seven to ten days earlier than the Redtop and has more highly colored skin.

2 Drawing Figures

BACKGROUND OF THE NEW VARIETY

The present invention relates to a new and distinct variety of peach tree which is generally similar to the Redtop Peach Tree (unpatented) of which it is a sport, but which bears fruit which is more highly colored than the Redtop and which ripens seven to ten days earlier.

The Redtop Peach Tree, developed by the United States Department of Agriculture and the Fresno State College Foundation, is well known as producing high quality, relatively early ripening peaches whose skin has an attractive blush and which have good fresh market acceptance. It is also well known that the time of harvest of commercially produced peaches greatly influences the price brought on the market, and an earlier ripening peach can generally be marketed at a higher price.

Further, consumer acceptance of a fresh market peach is greatly influenced by the skin coloration thereof, so that a highly colored skin is highly desirable for market. The present variety possesses the desirable qualities of the Redtop variety of peach tree but has the advantages of bearing fruit which is earlier ripening and has a more highly colored skin.

ORIGIN AND ASEXUAL REPRODUCTION OF THE NEW VARIETY

The new variety of peach tree was discovered by me as a sport growing in an orchard of Redtop peach trees owned by me near the City of Reedley, in the County of Fresno, in the State of Calif. Buds from the sport were budded by me at my above designated orchard, and the fruit and tree characteristics resulting from such budding proved identical to those of the original sport.

SUMMARY OF THE NEW VARIETY

The instant variety of peach tree is characterized by perpetuating the desirable characteristics of the Redtop Peach Tree, but has the important distinctions of ripening from seven to ten days earlier under the growing conditions prevailing in the San Joaquin Valley of California and of having skin with a more attractive coloration. The new peach tree bears freestone fruit having red striated yellow flesh. The skin of the fruit has an apricot (page 43, plate 10, H-7) background which is heavily blushed with red (Cuba+Wallflower, Page 35, Plate 6, L-10).

BRIEF DESCRIPTION OF THE DRAWING

The accompanying drawing is a color photograph of mature fruit of the subject variety, with two of the fruit divided on the suture plane showing the flesh color and the stone, together with two typical leaves.

DETAILED DESCRIPTION

Referring more specifically to the pomoligical details of this new and distinct variety of peach tree, the following has been observed under the ecological conditions prevailing in the designated orchard near Reedley, Calif. All major color code plate identifications are by reference to the *Dictionary of Color* by A. Maerz and M. Paul, second edition, published in 1950.

TREE

Size: Large.
Figure: Spreading.
Productivity: Very productive.
Bearing: Regular.
Trunk:
- *Diameter in relation to length.*—Stocky.
- *Surface characteristics.*—Smooth.

Branches:
- *Size.*—Large.
- *Surface character.*—Smooth.
- *Color.*—Cochin Moccasin+Argus Brown (Page 37, Plate 7, A-12).
- *Lenticels.*—Number — numerous. Size — 0.5×2.5 mm.

Leaves:
- *Size.*—Large.
- *Length.*—180 mm.
- *Width.*—40 mm.
- *Shape.*—Oval-lanceolate, narrowly-acuminate.
- *Color.*—Upper — Fir (Page 71, Plate 24, J-7). Lower — Lichen (Page 69, Plate 23, H-6).
- *Marginal form.*—Finely serrate.
- *Petiole.*—Length — 11 mm. Width — 2 mm.
- *Stem glands.*—Number — 2 to 4. Arrangement — variable. Size — 1×2 mm. Type — reniform. Color — Powdered Gold (Page 47, Plate 12, I-6).

Flower buds:
- *Size.*—Medium to large.
- *Shape.*—Obtuse to conical and plump.
- *Surface.*—Pubescent.

Flowers:

*Dates of bloom.*—First bloom noted on March 5. Ninety percent open — March 11. Petal fall — March 15.

*Size.*—Large, 40 mm in diameter when open.

*Color.*—Upper side — Pink (Page 121, Plate 49, E-1). Lower side — Pink (Page 121, Plate 41, F-1).

*Number of pistils and stamens.*—Pistils — 1; stamen — 38 to 40.

FRUIT

Maturity:

7 to 10 days before Redtop; 4½ to 5 weeks earlier than Elberta (unpatented).

Size:

*Uniformity.*—Uniform.

*Diameter.*—60 to 62 mm.

*Transverse in suture plane.*—64 to 66 mm.

*Transverse at right angles to suture plane.*—62 to 65 mm.

Form:

*Symmetry.*—Round oblong with unequal sides.

*Suture.*—Distinct, slightly depressed, deeper at apex, 87 to 92 mm in length.

*Ventril surface.*—Smooth.

*Stem cavity.*—Acute angle, medium in width and depth, 18 mm×25 mm×13 mm deep.

*Base.*—Shoulders rounded.

*Apex.*—Somewhat rounded with a pointed tip, slightly beaked.

*Pistil point.*—Cuspidate.

*Stem.*—Length — 10 mm. Width — 5 mm.

Skin:

*Thickness.*—Medium.

*Texture.*—Medium.

*Tendency to crack.*—None.

*Color.*—(Blush) Cuba+Wallflower (Page 35, Plate 6, L-10). (Ground) Apricot (Page 43, Plate 10, H-7).

*Pubescence.*—Medium amount and fine textured.

Flesh:

*Color.*—Yellow portion — Burnous (Page 41, Plate 9, J-4). Red striations — Canna Antique (Page 31, Plate 4, J-11).

*Flesh.*—Surface of pit cavity — Burnous (Page 41, Plate 9, J-4).

*Color of pit well.*—Burnous (Page 41, Plate 9, J-4).

*Juice.*—Juicy.

*Flavor.*—Sweet, subacid and pleasing.

*Aroma.*—Pleasing.

*Texture.*—Fine grained, tender and melting.

*Ripening.*—Even.

*Eating quality.*—Good.

Stone:

*Adhesion.*—Free.

*Size.*—Medium, 35 mm long and 22 mm in diameter.

*Form.*—Oval and beaked.

*Sides.*—Many deep pits and a few deep grooves.

*Sutures.*—Ventral: narrow, steep at edges and winged. Dorsal: narrow, slightly winged and shallowly grooved.

*Color.*—Rose Amber (Page 47, Plate 12, G-9).

*Tendency to split.*—None.

Use: Fresh.

Keeping quality: Good.

Shipping quality: Good.

Although the new variety of peach tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of peach tree, what is new and desired to be secured by Letters Patent is:

1. A new and distinct variety of peach tree substantially as illustrated and described, characterized by its bearing of freestone fruit having yellow flesh striated with red and by its general resemblance to the Redtop Peach Tree (unpatented), but which is distinguished therefrom by its fruit ripening from seven to ten days earlier and by having more highly colored skin.

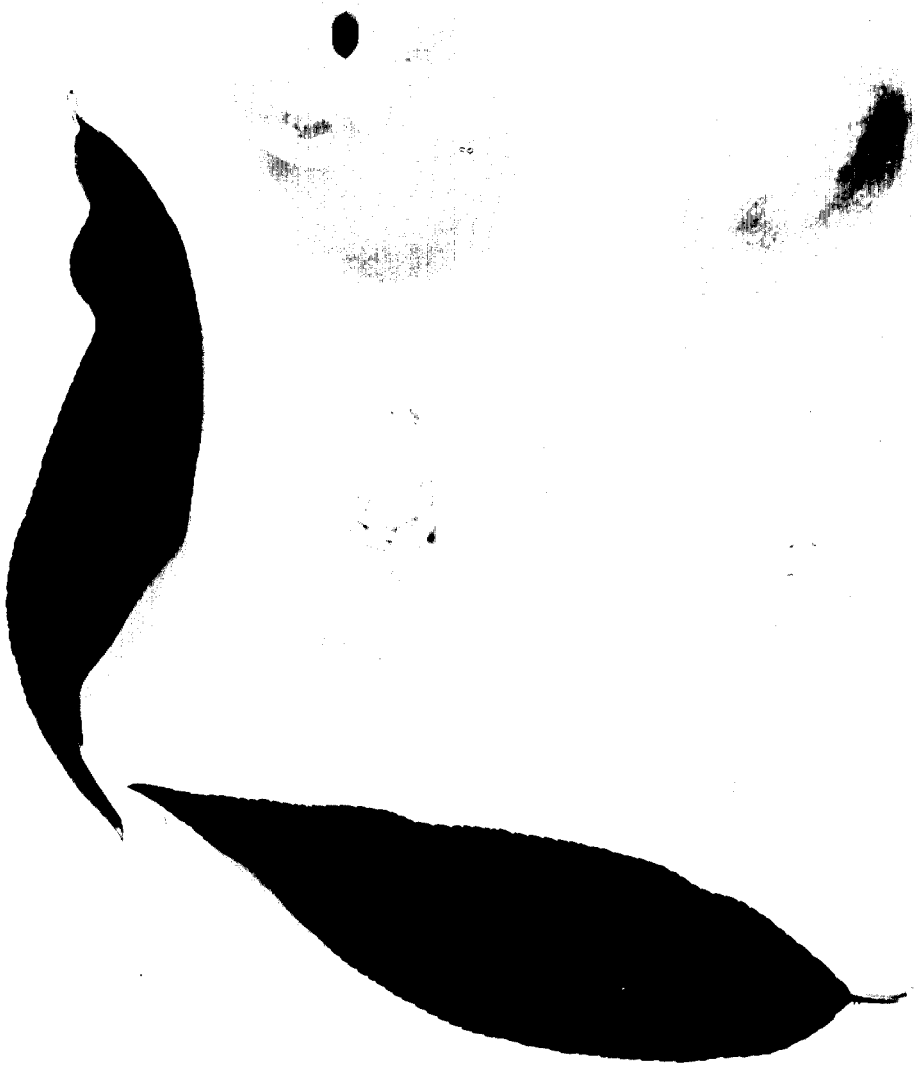

* * * * *